(12) United States Patent
Douglas et al.

(10) Patent No.: US 11,285,471 B2
(45) Date of Patent: Mar. 29, 2022

(54) PORTABLE CONTROLLED MICRO-ENVIRONMENT DEVICE FOR MODULAR BIO-PROCESSING

(71) Applicant: Nextern, Inc., White Bear Lake, MN (US)

(72) Inventors: Ryan Douglas, Stillwater, MN (US); Richard Farrell, Delwood, MN (US); David Bontrager, Minneapolis, MN (US)

(73) Assignee: Nextern Innovation, LLC, White Bear Lake, MN (US)

( * ) Notice: Subject to any disclaimer, the term of this patent is extended or adjusted under 35 U.S.C. 154(b) by 812 days.

(21) Appl. No.: 15/993,481

(22) Filed: May 30, 2018

(65) Prior Publication Data

US 2018/0369802 A1 Dec. 27, 2018

Related U.S. Application Data

(60) Provisional application No. 62/512,549, filed on May 30, 2017.

(51) Int. Cl.
*B01L 1/02* (2006.01)
*B01L 1/04* (2006.01)
(Continued)

(52) U.S. Cl.
CPC .............. *B01L 1/025* (2013.01); *B01L 1/04* (2013.01); *C12M 23/00* (2013.01); *F24F 3/16* (2013.01);
(Continued)

(58) Field of Classification Search
CPC .... B01L 1/025; B01L 1/04; B01L 9/52; B01L 2200/026; B01L 2200/0621; B01L 2200/0631; B01L 2200/0689; B01L 2200/147; B01L 2200/18; B01L 2300/23; C12M 23/00; F24F 3/16
See application file for complete search history.

(56) References Cited

U.S. PATENT DOCUMENTS

| 4,248,972 | A  | * | 2/1981  | Fischer | ................. | C12M 23/34 |
|           |    |   |         |         |                   | 435/294.1  |
| 2004/0248281 | A1 | * | 12/2004 | Wright  | ..................... | A01N 1/02  |
|           |    |   |         |         |                   | 435/284.1  |

(Continued)

*Primary Examiner* — William H. Beisner
*Assistant Examiner* — Danielle B Henkel
(74) *Attorney, Agent, or Firm* — Craige Thompson; Thompson Patent Law; Timothy D. Snowden

(57) ABSTRACT

Apparatus and associated methods relate to an adaptable microenvironment for cellular and biological processing in a traceable, transportable unit. In an illustrative example, an apparatus consists of one or more portable cell tissue containment modules that may be removably interconnected to perform a processing step and/or transfer the stored medium to another module. Associated apparatus and methods are proposed to ensure non-contaminating mechanical or fluid communication between a plurality of modules or between a module and peripheral equipment, to limit process errors such as steps performed out of order, and to intrinsically manage identification of tissue samples with accompanying process data in a manner that decreases risk of mislabeling or otherwise mishandling a sample at all stages of the production and treatment process.

20 Claims, 3 Drawing Sheets

(51) Int. Cl.
  *C12M 1/00*  (2006.01)
  *B01L 9/00*  (2006.01)
  *F24F 3/16*  (2021.01)

(52) U.S. Cl.
  CPC .......... *B01L 9/52* (2013.01); *B01L 2200/026* (2013.01); *B01L 2200/0621* (2013.01); *B01L 2200/0631* (2013.01); *B01L 2200/0689* (2013.01); *B01L 2200/147* (2013.01); *B01L 2200/18* (2013.01); *B01L 2300/023* (2013.01)

(56)       References Cited

U.S. PATENT DOCUMENTS

| | | | |
|---|---|---|---|
| 2009/0023608 A1* | 1/2009 | Hung | B01L 3/502761 506/32 |
| 2011/0124078 A1* | 5/2011 | Edwards | C12M 29/16 435/174 |
| 2017/0227525 A1* | 8/2017 | Griffith | B01L 3/502715 |
| 2020/0025782 A1* | 1/2020 | Ahlfors | B01L 1/04 |

* cited by examiner

PORTABLE CONTROLLED MICRO-ENVIRONMENT DEVICE FOR MODULAR BIO-PROCESSING

CROSS-REFERENCE TO RELATED APPLICATIONS

This application claims the benefit of U.S. Provisional Application Ser. No. 62/512,549 titled "Portable Controlled Micro Environment for Modular Bio-Processing," filed by Douglas, et al. on May 30, 2017.

This application incorporates the entire contents of the foregoing application(s) herein by reference.

TECHNICAL FIELD

Various embodiments relate generally to apparatuses and the associated methods to process cellular tissue in a manner that is modular, portable, and traceable.

BACKGROUND

Cellular therapy relies on costly clean room environments and surrounding infrastructure to process biological materials, which must be kept free of contamination and handled in controlled environmental conditions. Autologous treatments, for example, take cellular tissue from a patient, modify or otherwise process the tissue, and return the resulting sample to the same patient. The processes to produce these personalized treatments are conducted in clean room environments at work stations set up expressly for each step of the treatment production process.

SUMMARY

Apparatus and associated methods relate to an adaptable microenvironment for cellular and biological processing in a traceable, transportable unit. In an illustrative example, an apparatus consists of one or more portable cell tissue containment modules that may be removably interconnected to perform a processing step and/or transfer the stored medium to another module. Associated apparatus and methods are proposed to ensure non-contaminating mechanical or fluid communication between a plurality of modules or between a module and peripheral equipment, to limit process errors such as steps performed out of order, and to intrinsically manage identification of tissue samples with accompanying process data in a manner that decreases risk of mislabeling or otherwise mishandling a sample at all stages of the production and treatment process.

Various embodiments may provide one or more advantages. For example, some implementations may provide compact portable environments for handling and conveying biological cultures between clean room environments. Some examples permit tissues or other materials to be developed in an optimized growth chamber environment without restriction to a clean room or laboratory location. Such examples may improve efficiency and reduce cost, while increasing flexibility and mobility, which may be particularly valuable in time-sensitive applications (e.g., life saving medical scenarios such as transplants). Quick connections may be made via access port(s) that may, for example, permit rapid connection and communication of media in a chamber to another chamber or source of nutrients, for example.

In various embodiments, a micro environment controls biological purity of its contents while it is outside a larger clean room environment, the accessories control operations that mediate between the micro environment's contents, transfer methods and couplings control purity of the sample in transitional stages, and data tracking controls traceability of both the sample and the treatment process it undergoes.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

A portable chamber system is proposed comprising an internal volume that is releasably sealed from the passage of biological matter between the interior of the chamber and the exterior world. Embodiments of the system may comprise one or more different micro environment chamber designs. Each may be optimized for specific steps of the processes involved in cellular autologous therapies, such as expansion, separation, counting, preservation, and any requisite intermediate steps.

Figure 1:
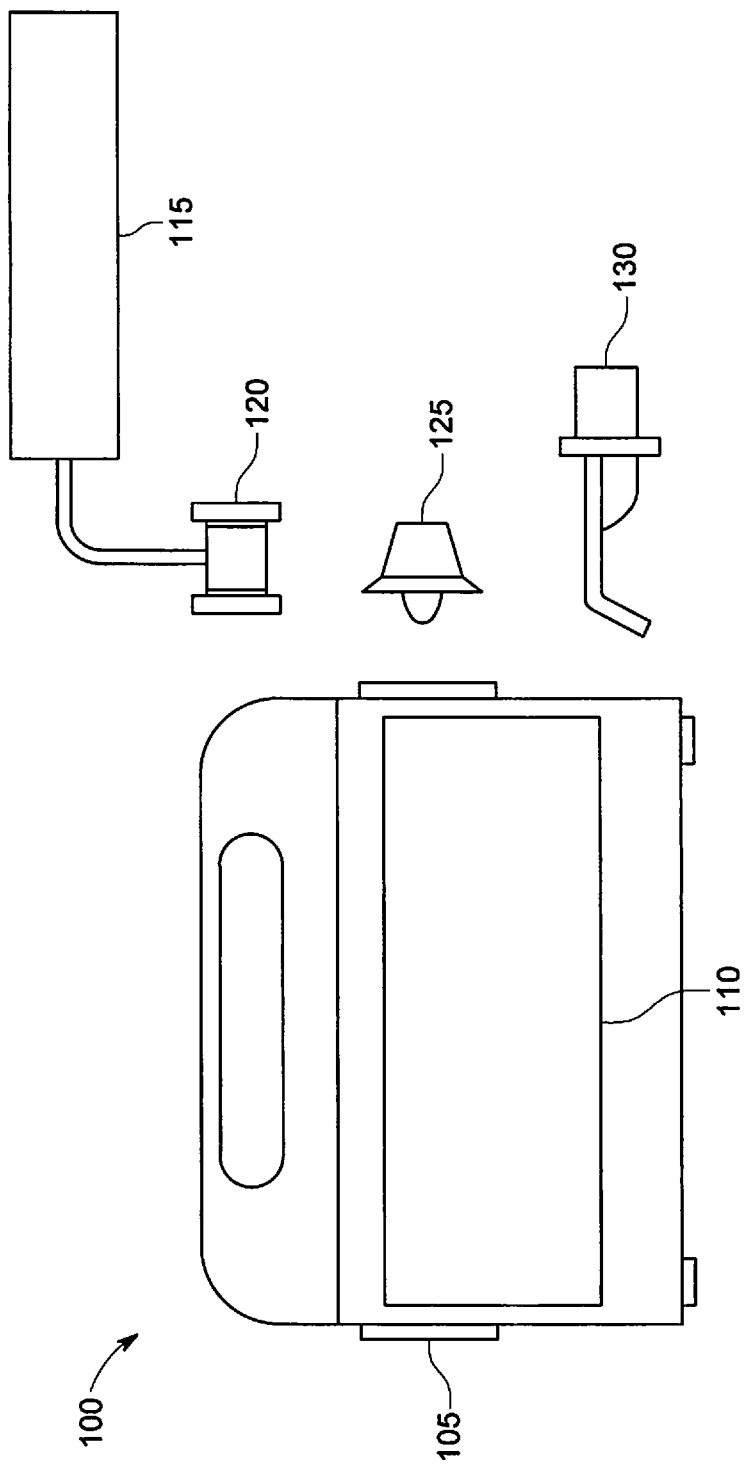
FIG. 1 depicts a front perspective of an exemplary transportable microenvironment with various accessories.

FIG. 1 depicts a front perspective of an exemplary transportable microenvironment with various accessories. The portable microenvironment [100], aside from the main body of the microenvironment, is further constructed of an access port [105] and a viewing port [110]. The access port [105] is used with various accessories. For example, the various accessories may be a differential pressure accessory [120] that is connected to an external pressure source [115], a decontamination accessory [125], or an extraction/insert accessory [130]. The differential pressure accessory [120] may help to create or maintain a vacuum or may be used to introduce or eliminate various elements through partial pressures, for example. The decontamination accessory may, for example, introduce ultraviolet light into the portable microenvironment [100] to sterilize the environment. The extraction/insertion accessory [130] may introduce new elements or nutrients into the portable microenvironment [100] through the use of external devices such as a pump or syringe, for example. The adaptable accessory port [105] and the portable nature of the portable microenvironment [100] advantageously allow the apparatus to be used in various locations and for diverse purposes.

For example, the apparatus in FIG. 1 may portably, modularly contain and process cell tissue in cellular therapy processes. Access ports on the side of the apparatus may provide releasable connections to other similar or identical modules, or to a variety of accessories with different functions. When no connection is made, the access port may be sealed to decouple the module interior from the external environment. Access ports may be installed with a filter similar to a HEPA filter to allow contamination-free pressure equalization between the module interior and the external environment.

In various embodiments, a transportable microenvironment may be constructed to releasably connect with various accessories. In one example, the accessory may be a decontamination coupling where the decontamination coupling may be shaped to insert partially or fully into a micro environment with the access port open to expose the full interior of the chamber to the sanitizing medium, e.g. UV radiation or a sanitizing fluid such as 70% isopropyl or high temperature steam. In another example, the decontamination coupling may be configured to mate with an access port that is still closed so as to decontaminate the access port's exterior surfaces before the port is opened. In one example, the accessory may be a wand that can perform injection and/or extraction to move fluid into and/or out of the micro environment to, for example, inoculate a prepared growth medium with living cells that are to be propagated, or to, in another example, extract a sample of cell-bearing medium to estimate a cell count and monitor the cell expansion process. This coupling may also be used to inject/extract large or small quantities of e.g. cell growth medium or carbon dioxide gas into/from the chamber. The coupling may interface with the access port in a fluid-impermeable manner. It may further contain a passage for air through the coupling wall to allow pressure to equalize between the interior and exterior of the chamber as fluids are added or removed. In one example, the accessory may be a stirring or agitation wand and a sensor or sensor cluster wand. In one example, the accessory may implement and/or effect automated processes to perform steps that do not require human intervention.

In some implementations, a kit may be formed to include, for example, a transportable microenvironment and a set of accessories in a package. The package may include a set of instructions for use of the transportable microenvironment and each of the accessories in the set. The kit may include one or more mechanisms for tracking, in accordance with various examples described elsewhere herein.

Figure 2:
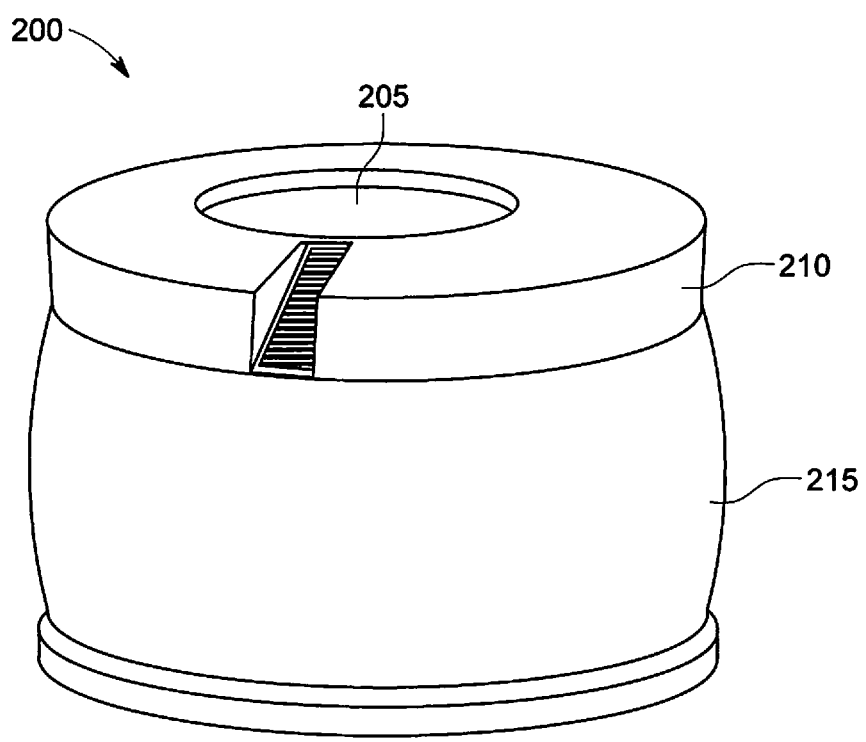
FIG. 2 depicts an exemplary portable microenvironment suitable for use in a centrifuge.

FIG. 2 depicts an exemplary portable microenvironment suitable for use in a centrifuge. The exemplary cylindrical portable microenvironment [200] is constructed with a viewing window [205], a removable lid [210], and a cylindrical or curved containment unit body [215]. The sealable and removable lid [210] may engage with the containment unit body [215] through a threaded mechanism or another, similar locking mechanism, for example. The sample inside of the cylindrical portable microenvironment [200] may be monitored using the viewing window [205]. The environment inside of the portable microenvironment may be maintained using a filtration device, such as a HEPA filter, by example. The cylindrical portable microenvironment [200] has a cylindrical or curved containment body unit [215] for optimal use with a centrifuge.

In another example, the apparatus in FIG. 2 may be constructed to portably, modularly handle and process cell tissue in cell therapy processes. This embodiment may be fitted with a top and/or bottom access port. If no connection is made the access port(s) may be sealed to decouple the module interior from the external environment. This embodiment may be integrally fitted with a HEPA or similar filter to allow contamination-free pressure equalization between the module interior and the external environment.

Figure 3:
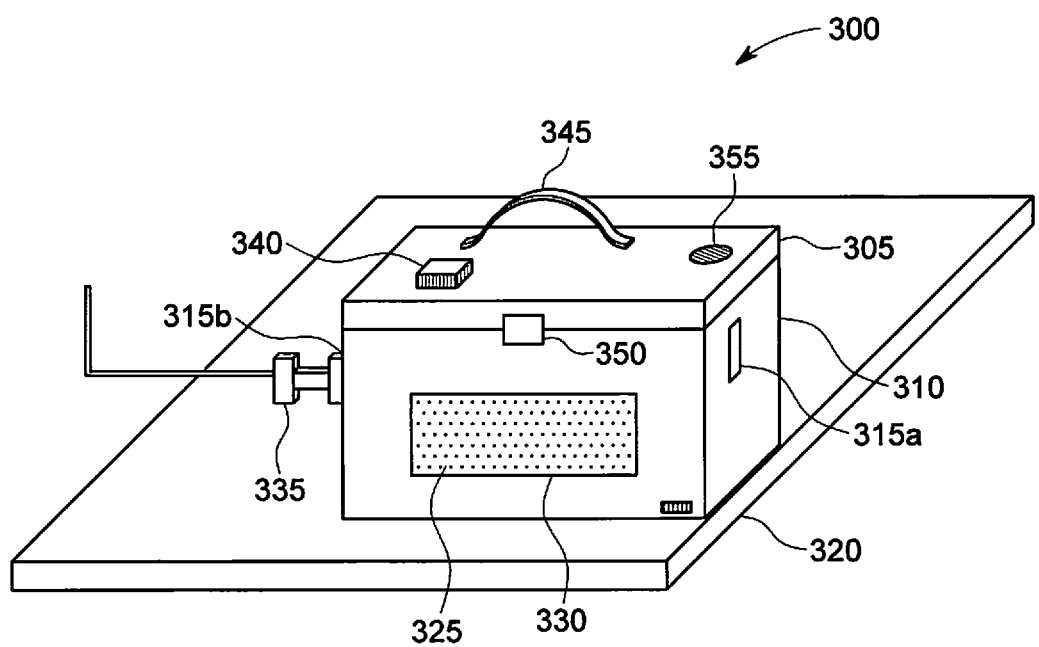
FIG. 3 depicts a front perspective of an exemplary portable microenvironment in use on a laboratory bench.

FIG. 3 depicts a front perspective of an exemplary portable microenvironment in use on a laboratory bench. The portable microenvironment [300] is constructed of a sealable lid [305] and a containment unit body [310], with at least one access port [315a-315b]. The portable microenvironment [300] may be used on various surfaces or at various locations, such as a laboratory benches [320] because it advantageously maintains a clean or optimal environment inside of the containment unit body [310]. Additionally, the portable microenvironment [300] advantageously allows for various processes to be conducted to the biological sample [325] accessed through one of the various accessory ports [315a-b]. Various containment unit accessories [335] may engage with an accessory port [315a-b] to aspirate or eliminate various materials into the sealed containment unit body [310]. The biological sample [325] can be viewed and monitored from the viewing window [330]. As the portable microenvironment [300] is transported to various locations or as various processing steps are conducted upon the biological sample [325], the tracking mechanism [340] may be used to log the various steps or various locations in a database. The portable microenvironment [300] is advantageously further constructed with a handle [345], for ease of transportability. The handle [345] may be fixed to the sealable lid [305] or may be detachable. The sealable lid [305] engages with the containment unit body [310] and is fixed to the containment unit body [310] with at least one locking mechanism [350]. Once sealed, the pressure and environment inside of the portable microenvironment [300] is additionally adjusted or maintained using a filtration mechanism [355]. The filtration mechanism [355] may be a standard filtration device, such as a HEPA filter. These embodiments have the benefit of creating a traceable, portable microenvironment whose environment may be maintained and adjusted easily.

Although various embodiments have been described with reference to the FIGS., other embodiments are possible. For example, an alternative embodiment may use various tracking mechanism technologies. The tracking mechanism technologies may use a Bluetooth connection technology, a wireless connection technology, a scannable bar code, or an RFID mechanism. An alternative embodiment may allow for the handle to detach. An alternative embodiment may allow for an inner and outer chamber for the portable microenvironment. Some processing steps may require the portable containment unit to be processed or filled in a clean room environment. The portable containment unit may maintain the clean room environment within the containment unit body.

For example, a transportable microenvironment may be constructed with various access ports providing physical communication between the interior and exterior of the micro environment. These access ports may be sealed in a manner that provides an impermeable barrier to biological agents on either side of the barrier. Access ports may additionally be designed such that the geometry allows reliable decontamination with methods such as UV exposure, chemical sanitization (e.g. with a 70% isopropyl solution), or steam-based sterilization. In another example, a transportable microenvironment may be constructed with installed sensors or receptacles for temporarily connected sensors to monitor status of the micro environments' internal chamber. If, alternatively, sensors are permanently installed, their values may be obtained by releasably connecting a readout monitor's data input to the sensor outputs and/or by reading a display that is integral to the micro environment. In another example, a transportable microenvironment may be constructed with material composition that is optimized for one or more specific steps, such as low temperature resistance for micro environments that will undergo cryogenic preservation, and/or for processes that all micro environments will experience such as sterilization.

In another example, a transportable microenvironment may be constructed to have an internal geometry allowing for decontamination. The internal geometry may be such that a UV source placed at or in an access port can illuminate all internal surfaces. In another example, a transportable microenvironment may be constructed with one or more optically transparent surfaces integral to the micro environment walls to allow visual evaluation and optionally measurement of some optical properties of the contained bio matter. In another example, a transportable microenvironment may be constructed with an integral or detachable carrying handle or external shape and size that allows the micro environment to be carried by users. In another example, a transportable microenvironment may be constructed with a releasably sealable lid that provides substantial access to the micro environment interior for the purposes of cleaning, servicing, or performing bio-processing steps with greater access than that provided by the access ports. While many processes may not require a clean room, some embodiments may allow this greater access for steps that are simplified when performed in a clean room. In another example, a transportable microenvironment may be constructed with a high granularity air filter such as a HEPA filter to let pressure equalize between the interior and exterior of the micro environment while maintaining the integrity of the contained biological tissue.

In another example, a transportable microenvironment may be constructed to aid in access and transfer, some portion of the micro environment interior may comprise a removable enclosed or non-enclosed container that holds some or all of the medium that the micro environment may contain. Some embodiments may be designed for particularly high thermal transfer between the contained fluid and the exterior world to provide ease of temperature control in a larger temperature-controlled environment e.g. a cryogenic chamber. Some embodiments may incorporate particularly low thermal transfer to provide extended time at a chosen temperature once the micro environment has been removed from the temperature-controlled environment for transport. In another example, a transportable microenvironment may be constructed so that the micro environments and/or the installed access ports may provide integral fluid connection ports to e.g. inject gas of a desired composition at a desired positive or negative pressure into the micro environment with the contained fluid.

In another example, a transportable microenvironment may be constructed to releasably connect with various accessories. In one example, the accessory may be a decontamination coupling where the decontamination coupling may be shaped to insert partially or fully into a micro environment with the access port open to expose the full interior of the chamber to the sanitizing medium, e.g. UV radiation or a sanitizing fluid such as 70% isopropyl or high temperature steam. In another example, the decontamination coupling may be configured to mate with an access port that is still closed so as to decontaminate the access port's exterior surfaces before the port is opened. In one example, the accessory may be a wand that can perform injection and/or extraction to move fluid into and/or out of the micro environment to, for example, inoculate a prepared growth medium with living cells that are to be propagated, or to, in another example, extract a sample of cell-bearing medium to estimate a cell count and monitor the cell expansion process. This coupling may also be used to inject/extract large or small quantities of e.g. cell growth medium or carbon dioxide gas into/from the chamber. The coupling may interface with the access port in a fluid-impermeable manner. It may further contain a passage for air through the coupling wall to allow pressure to equalize between the interior and exterior of the chamber as fluids are added or removed. In one example, the accessory may be a stirring or agitation wand and a sensor or sensor cluster wand. In one example, the accessory may implement and/or effect automated processes to perform steps that do not require human intervention.

In another example, a transportable microenvironment may be constructed to accommodate transfer of biological samples from one micro environment to another or between a micro environment and assorted peripheral equipment. A transfer coupling is proposed to provide seals from one micro environment's access port to the object with which it will exchange fluids. The transfer coupling may seal in a manner that is impermeable to biological agents. In another example, a transportable microenvironment may be constructed with a transfer coupling using a positive or negative pressure as induced by a pneumatic pump to drive fluids from one volume to another. Other embodiments may employ contact-free pumps such as a peristaltic pump. In another example, a transportable microenvironment may be constructed with access ports on one or more chamber sidewalls, the top wall, and/or the bottom of the chamber.

In another example, a transportable microenvironment may be constructed with appropriate geometry to enable stacking for storage and/or with couplings that releasably interconnect on the respective top and bottom of the stacked units, providing a direct gravity feed flow path between the two micro environments. Some embodiments may allow additional equipment to be placed between two units that are vertically stacked to e.g. filter, measure properties of, or perform a separation step on the flowing medium. Access ports located appropriately on a micro environment sidewall may also allow gravity actuated transfers.

Furthermore, in one embodiment, the process used to trace the portable microenvironment may be implemented independently. For this method, a since the portable microenvironment may be transported to various locations, it may be easier to lose track of samples or of the process steps. Therefore, the portable microenvironment may also have a tracking mechanism. This tracking mechanism may be on both the removable lid and the containment unit body or either, depending on the use. Step 1 is to install the various tracking mechanisms on the portable containment unit. Step 2 is to scan or connect the various tracking mechanisms to a computer processing system. Step 3 is to link the portable containment unit to a specific sample or patient. Step 4 is to scan or log the specific locations or processing steps of the portable containment unit and the sample therein. Step 5 results in reports providing data on process executed on sample, chain of custody of the sample, and maintenance information for the portable microenvironment and the sample therein.

In another example, a transportable microenvironment tracking process may be used involving unique identifiers assigned to each micro environment. These identifiers may be provided as a human readable label, or as a machine-readable code such as an RFID tag or a barcode. In another example, a transportable microenvironment tracking process may process data or may connect with a computer or network database. Some embodiments may implement a system wherein scanning a micro environment's unique identifier will access the remotely stored data for e.g. review. Some embodiments of the tracking system will embed process data in an electronic storage format that is integral to the micro environments or connected to the micro environments in such a way that there is good certainty that a storage unit will reliably travel with its assigned micro environment. Electronic data may be retrieved or added to via wireless or wired methods.

In another example, a transportable microenvironment tracking process may compile a process history that travels with each particular sample. When samples are transferred between containers, the data is also transferred to the device that receives the biological sample. Each processing step may require entry of e.g. operator identifier and accordingly record in the electronic data process information such as what step was performed, who performed it, when it was performed, and other pertinent data. Example data that may be recorded includes: Operator name or ID; Date and time of operation; Prescribed treatment for a given sample; Identifier of patient for whom the sample is being processed; Steps already performed; Results and parameters of each step, including results of measurements; Step(s) to follow the current step; Equipment data such as micro environment identifiers, calibration dates of measurement equipment, sterilization dates of sterile equipment, etc; or other pertinent data that may aid in conducting the treatment.

In another example, a transportable microenvironment tracking process may restrict access to some or all of this data to certain authorized operators or methods of access, while some information (e.g. current and/or next step) may be displayed on an integral display. In another example, a transportable microenvironment tracking process may enable automated checks may control the sequence of the process's steps. Some embodiments may prevent steps from being performed outside of a certain order by halting operation or by providing an indicator or warning to the user that they are about to perform an unexpected or undesired action. Data tracking may additionally follow the treatment back to the patient where a system might compare sample data with patient data to verify that the correct treatment has been directed to that patient.

In another example, a transportable microenvironment tracking process may account for differences in design or physical construction for the different steps. For example, there may be differing access port design or differing connection elements that disagrees with the established sequence. In another example, a transportable microenvironment tracking process may, in a process with steps A through D, chamber design B might be able to connect its output to the input of chamber design C, but not to the input of chamber design D. Some embodiments may allow for generalized processing where no restrictions are placed on connection sequence. In another example, a transportable microenvironment tracking process may be programmed to reduce human error while generalization reduces process development cycles by providing automated steps that can be configured in a desired order without reprogramming larger, expensive equipment or specialized, individual workstations, thus both the equipment and the process is modularized.

Some aspects of embodiments may be implemented as a computer system. For example, various implementations may include digital and/or analog circuitry, computer hardware, firmware, software, or combinations thereof. Apparatus elements can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Some embodiments may be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example and not limitation, both general and special purpose microprocessors, which may include a single processor or one of multiple processors of any kind of computer. Generally, a processor will receive instructions and data from a read-only memory or a random-access memory or both. The essential elements of a computer are a processor for executing instructions and one or more memories for storing instructions and data. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits). In some embodiments, the processor and the member can be supplemented by, or incorporated in hardware programmable devices, such as FPGAs, for example.

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. An exemplary embodiment may be implemented in a computer system that includes a graphical user interface and/or an Internet browser. To provide for interaction with a user, some implementations may be implemented on a computer having a display device, such as an LCD (liquid crystal display) monitor for displaying information to the user, a keyboard, and a pointing device, such as a mouse or a trackball by which the user can provide input to the computer.

In various implementations, the system may communicate using suitable communication methods, equipment, and techniques. For example, the system may communicate with compatible devices (e.g., devices capable of transferring data to and/or from the system) using point-to-point communication in which a message is transported directly from a source to a receiver over a dedicated physical link (e.g., fiber optic link, infrared link, ultrasonic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, and the computers and networks forming the Internet. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, FireWire, ATA/IDE, RS-232, RS-422, RS-485, 802.11 a/b/g/n, Wi-Fi, WiFi-Direct, Li-Fi, BlueTooth, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

In various embodiments, a computer system may include non-transitory memory. The memory may be connected to the one or more processors may be configured for encoding data and computer readable instructions, including processor executable program instructions. The data and computer readable instructions may be accessible to the one or more processors. The processor executable program instructions, when executed by the one or more processors, may cause the one or more processors to perform various operations.

In various embodiments, the computer system may include Internet of Things (IoT) devices. IoT devices may include objects embedded with electronics, software, sensors, actuators, and network connectivity which enable these objects to collect and exchange data. IoT devices may be in-use with wired or wireless devices by sending data through an interface to another device. IoT devices may collect useful data and then autonomously flow the data between other devices.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A transportable bio-chamber used to maintain sterile environments comprising:
   a first enclosure and a second enclosure, each enclosure comprising:
      at least one outer wall defining an interior chamber with an opening, the at last one outer wall being configured to receive a lid to cover the opening to seal the chamber from ambient atmosphere, wherein the chamber is adapted to maintain a sterile environment when the lid is sealed to cover the opening; and,
      at least one access port disposed in the at least one outer wall and configured to selectively provide fluid communication between the chamber and an exterior ambient environment; and,
   at least one tracking object coupled to the enclosure, the tracking object comprising information associated with the enclosure in a remote database,
   wherein the enclosure further comprises a viewing window configured to permit monitoring of contents in the chamber while the chamber is sealed, wherein the enclosure is dimensioned for hand-carrying by one person, and
   wherein the first enclosure and the second enclosure are configured such that, in a transfer mode, the first enclosure is disposed on a top surface of the second enclosure and the respective at least one access ports are releasably interconnected via at least one transfer coupling to establish a direct gravity feed flow path such that the respective interior chambers are in fluid communication such that, after a seal impermeable to biological agents is established between the respective at least one access ports, contents from the chamber of the first enclosure are transferred to the chamber of the second enclosure by a gravity actuated transfer while controlling purity of the contents.

2. The apparatus of claim 1, further comprising a handle fixable to an exterior surface of the enclosure.

3. The apparatus of claim 1, wherein the at least one tracking object is fixed to an exterior of the enclosure.

4. The apparatus of claim 3, where the at least one tracking object is further operably connectable to a remote database configured to log activity associated with the chamber.

5. The apparatus of claim 1, wherein the at least one access port is configured to maintain a sterile environment by occluding fluid communication unless the at least one access port is engaged by a user.

6. The apparatus of claim 1, wherein the at least one access port further comprises a HEPA filtration device.

7. The apparatus of claim 1, further comprising at least one accessory configured for insertion through the at least one access port from an exterior into the chamber.

8. The apparatus of claim 7, wherein the at least one accessory comprises a differential pressure device to introduce or eliminate predetermined gaseous elements to the chamber.

9. The apparatus of claim 7, wherein the at least one accessory comprises a decontamination device adapted to sterilize the chamber.

10. The apparatus of claim 7, wherein the at least one accessory comprises a syringe pump configured to aspirate materials from the chamber to an exterior of the chamber.

11. A transportable bio-chamber used to maintain sterile environments comprising:
   a first enclosure and a second enclosure each comprising:
      at least one outer wall defining an interior chamber with an opening, the at least one outer wall being configured to receive a lid to cover the opening to seal the chamber from ambient atmosphere, wherein the chamber is adapted to maintain a sterile environment when the lid is sealed to cover the opening;
      at least one access port disposed in the at least one outer wall and configured to selectively provide fluid communication between the chamber and an environment exterior to the chamber; and,
   wherein the enclosure is dimensioned for hand-carrying by one person, and
   wherein the first enclosure and the second enclosure are configured such that, in a transfer mode, the first enclosure is disposed on a top surface of the second enclosure and the respective at least one access ports are releasably interconnected via at least one transfer coupling to establish a direct gravity feed flow path such that the respective interior chambers are in fluid communication such that contents from the chamber of the first enclosure are transferred to the chamber of the second enclosure by a gravity actuated transfer.

12. The apparatus of claim 11, further comprising a handle fixable to an exterior surface of the enclosure.

13. The apparatus of claim 11, wherein at least one tracking object is fixed to an exterior of the enclosure, the tracking object comprising information associated with the enclosure in a remote database.

14. The apparatus of claim 13, where the at least one tracking object is further operably connectable to a remote database configured to log activity associated with the chamber.

15. The apparatus of claim 11, wherein the at least one access port is configured to maintain a sterile environment by occluding fluid communication unless the at least one access port is engaged by a user.

16. The apparatus of claim 11, wherein the at least one access port further comprises a HEPA filtration device.

17. The apparatus of claim 11, further comprising at least one accessory configured for insertion through the at least one access port from an exterior into the chamber.

18. The apparatus of claim 17, wherein the at least one accessory comprises a differential pressure accessory device to introduce or eliminate predetermined gaseous elements to the chamber.

19. The apparatus of claim 17, wherein the at least one accessory comprises a decontamination accessory device adapted to sterilize the chamber.

20. The apparatus of claim 17, wherein the at least one accessory comprises a syringe pump configured to aspirate materials from the chamber to an exterior of the chamber.

* * * * *